United States Patent
Diamond et al.

(10) Patent No.: US 8,030,942 B2
(45) Date of Patent: Oct. 4, 2011

(54) METHOD AND APPARATUS FOR PROVIDING STABLE VOLTAGE TO ANALYTICAL SYSTEM

(75) Inventors: Steven Diamond, Somerville, MA (US);
Martin Forest, Nashua, NH (US);
Baoguo Wei, Salem, NH (US)

(73) Assignee: Agamatrix, Inc., Salem, NH (US)

( * ) Notice: Subject to any disclaimer, the term of this patent is extended or adjusted under 35 U.S.C. 154(b) by 999 days.

(21) Appl. No.: 11/937,196

(22) Filed: Nov. 8, 2007

(65) Prior Publication Data

US 2008/0073224 A1 Mar. 27, 2008

Related U.S. Application Data

(63) Continuation of application No. 10/907,806, filed on Apr. 15, 2005, now Pat. No. 7,372,277.

(51) Int. Cl.
*G01N 27/02* (2006.01)
(52) U.S. Cl. .......................... 324/444; 205/775
(58) Field of Classification Search ............. 324/73.1, 324/444, 71.1; 204/224 M
See application file for complete search history.

(56) References Cited

U.S. PATENT DOCUMENTS

| | | | |
|---|---|---|---|
| 4,206,028 A * | 6/1980 | Inoue .................. | 204/224 M |
| 4,659,435 A | 4/1987 | Brothers et al. | |
| 4,999,582 A | 3/1991 | Parks et al. | |
| 5,334,304 A | 8/1994 | Maget | |
| 5,891,409 A | 4/1999 | Hsiao et al. | |
| 5,994,878 A | 11/1999 | Ostergaard et al. | |
| 6,096,449 A | 8/2000 | Fuglevand et al. | |
| 6,176,989 B1 | 1/2001 | Shi | |
| 6,292,690 B1 | 9/2001 | Petrucelli et al. | |
| 6,353,324 B1 | 3/2002 | Uber, III et al. | |
| 6,387,556 B1 | 5/2002 | Fuglevand et al. | |
| 6,414,318 B1 | 7/2002 | Uber, III et al. | |
| 6,428,918 B1 | 8/2002 | Fuglevand et al. | |
| 6,646,415 B1 | 11/2003 | Nebrigic et al. | |
| 6,773,839 B2 | 8/2004 | Fuglevand et al. | |
| 6,811,903 B2 | 11/2004 | Vartak et al. | |
| 6,858,335 B2 | 2/2005 | Schmidt et al. | |
| 2003/0178322 A1 | 9/2003 | Iyengar et al. | |
| 2004/0220752 A1 | 11/2004 | Gopal | |
| 2005/0069892 A1 | 3/2005 | Iyengar et al. | |
| 2005/0212585 A1 | 9/2005 | Kerth et al. | |

FOREIGN PATENT DOCUMENTS

| | | |
|---|---|---|
| WO | 03/060154 A2 | 7/2003 |
| WO | 03/069304 A2 | 8/2003 |
| WO | 2005/022143 A2 | 3/2005 |

* cited by examiner

*Primary Examiner* — Vincent Q Nguyen
(74) *Attorney, Agent, or Firm* — Larson & Anderson, LLC

(57) ABSTRACT

An electrochemical cell has two terminals. One of the terminals is connected to a pulse-width-modulated (PWM) power supply and to a voltmeter. The other terminal is connected to circuitry capable of switching between amperometric and potentiometric measurement modes. A sequence of successive approximations permits selection of a PWM duty cycle giving rise to a desired voltage at the terminal connected with the power supply. In this way a stable excitation voltage is supplied to the cell even in the face of supply voltage instability or drift or instability in electronics coupled with the cell.

4 Claims, 1 Drawing Sheet

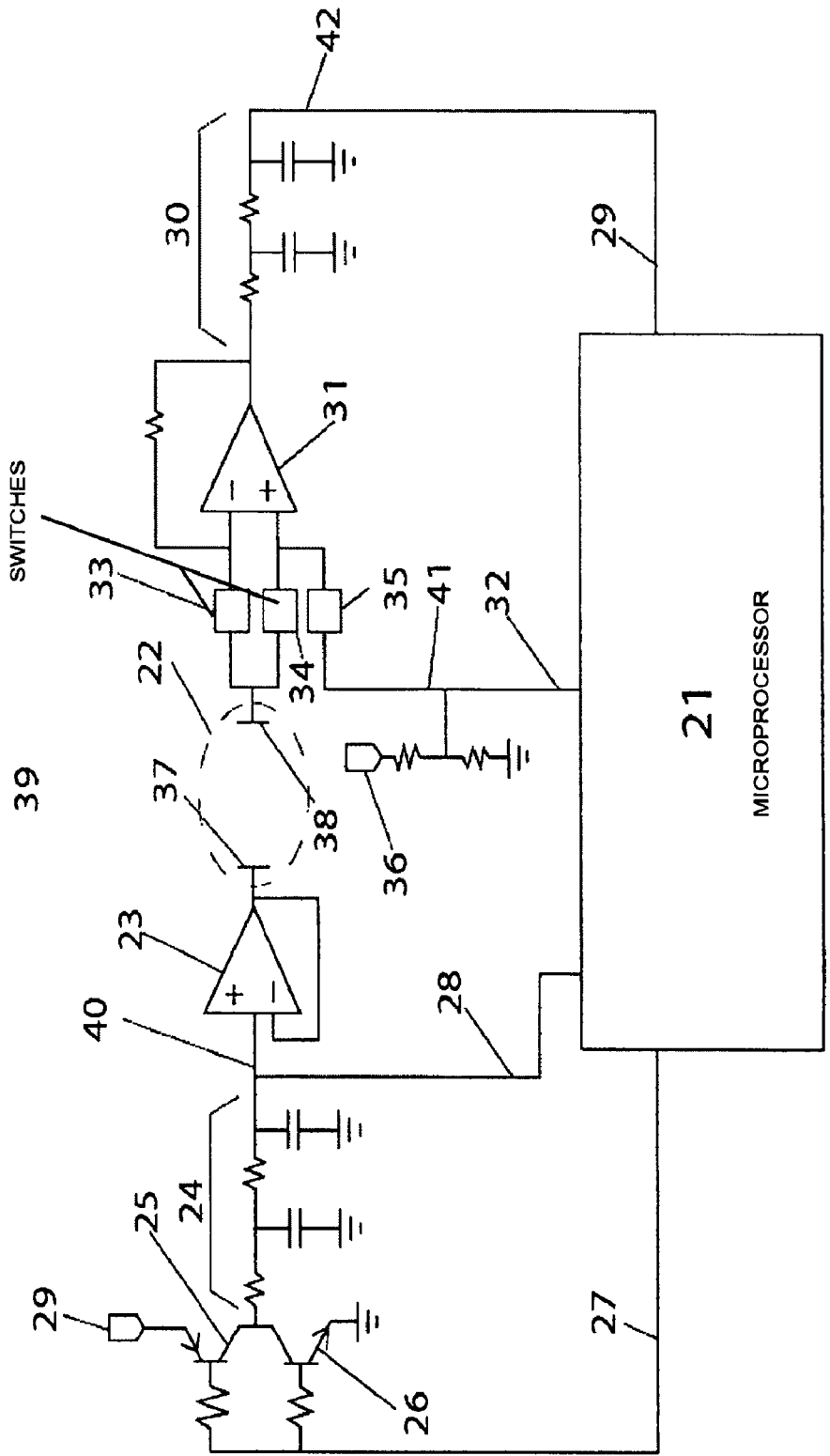
Figure

METHOD AND APPARATUS FOR PROVIDING STABLE VOLTAGE TO ANALYTICAL SYSTEM

BACKGROUND

It is not easy to make repeatable and accurate measurements in analytical systems such as consumer devices using an electrochemical cell. Many constraints contribute to the difficulty of this task. The consumer device must be light in weight, small and reliable. The price cannot be too high. The device may be running on a new battery or an old one, and the user cannot be relied upon to perform manual calibration steps. The repeatability and accuracy of the measurements must be preserved even in the face of temperature changes and user decisions such as whether or not to use a display backlight.

SUMMARY OF THE INVENTION

An electrochemical cell has at least two terminals. One of the terminals is connected to a pulse-width-modulated (PWM) power supply and to a voltmeter. Another of the terminals is connected to circuitry capable of switching between amperometric and potentiometric measurement modes. A sequence of successive approximations permits selection of a PWM duty cycle giving rise to a desired voltage at the terminal connected with the power supply. In this way a stable excitation voltage is supplied to the cell even in the face of supply voltage instability or drift or instability in electronics coupled with the cell.

DESCRIPTION OF THE DRAWING

The FIGURE shows an exemplary circuit according to the invention.

DETAILED DESCRIPTION

The FIGURE shows an analytical system 39 with an electrochemical cell 22. The analysis is performed under the control of a microcontroller 21. The microcontroller 21 has a pulse-width-modulated output 27 as well as analog inputs 28, 32 and 29. The analog inputs 28, 32, 29 are (in an exemplary embodiment) connected by means of a multiplexer internal to the microcontroller 21 to an analog-to-digital converter also internal to the microcontroller 21.
PWM signal 27 controls transistors 25, 26 which, through filter 24, develop a voltage at point 40 (called V2) from input 290. This voltage passes through buffer 23 to electrode 37 which, in an exemplary embodiment, is a working electrode. The voltage V2 can be measured by the microcontroller 21 via line 28.

The other electrode 38 of the cell 22 (which in an exemplary embodiment is a counter electrode) is connected by switches 33, 34, 35 to a reference voltage VREF (from input 36) at point 41 and to an operational amplifier 31. The voltage at point 41 can be measured by the microcontroller via line 32.

Depending on the positions of switches 33, 34, 35, the amplifier 31 is able to serve as a voltmeter or an ammeter. When it serves as an ammeter it is measuring the current through electrode 38 and thus through the reaction cell 22, and it gives rise to a voltage at point 42 that is indicative of the current. When it serves as a voltmeter it is measuring the voltage at electrode 38, and this gives rise to a voltage at point 42 that is indicative of the voltage. In either case, the microcontroller 21 is able, via line 29, to measure the voltage at point 42. Low-pass filter 30 is provided.

As a first step, the microcontroller 21 measures the voltage at the counter electrode 38. This measurement is relative to the working electrode 37, meaning that the microcontroller 21 will need to measure the voltages on lines 28 and 29 nearly contemporaneously.

It will be appreciated that both of the operational amplifiers 23, 31 are on the same chip. Thus to a first approximation the offsets and temperature drifts for the two op amps are likely to be about the same.

Next the microcontroller 21 guesses at a PWM duty cycle that may give rise to a desired voltage at the working electrode 37. (The choice of an initial duty cycle may be pre-configured in the microcontroller firmware or may be based upon past experience.) The duty cycle is applied and time is allowed to pass so that the PWM filtered voltage is stable.

Next the microcontroller 21 measures the voltage at 40 again. If the voltage at 40 is higher or lower than desired, then in a recursive way the PWM duty cycle is adjusted to come closer to the desired voltage at 40.

This cycle may be repeated several times.

In the case where the apparatus is being used to analyze a bodily fluid or other analyte, this sequence takes place:

Before the analyte has been introduced into the cell, V2 (the voltage at 40) is calibrated. The voltage V1 (the voltage at 41) is monitored.

Next the analyte is introduced into the cell 22. The microcontroller 21 performs the calibration again. It monitors V2. It monitors V1. The microcontroller 21 measures the output of the second op amp 31. In this way analytical measurements are carried out with respect to the analyte in the cell 22.

This sequence of events may be carried out as described in copending U.S. application Ser. No. 10/907,790, which application is hereby incorporated herein by reference for all purposes.

An exemplary sequence of steps will now be described in greater detail. These steps make the following assumptions.

The offset is assumed to be stable after the calibration sequence.

The offset of the two amplifiers is assumed to be the same because they are on the same chip and are under the same conditions.

The potential at the working electrode 37 is assumed to be the voltage at 28 plus the offset.

The potential at the counter electrode 38 is assumed (during sample introduction, recalibration, and amperometry) to be the same as the voltage at 32.

The potential at the counter electrode 38 is assumed (during potentiometry) to be the same as the voltage at 29, minus the offset.

Calibration. During a calibration phase, switch 35 is on and switches 33 and 34 are off. The PWM is adjusted so that the desired applied voltage is developed. Eventually the voltage at 40 is stable. The microcontroller also monitors any changes in the voltage at 32, and measures the voltage at 29. The difference between the two is the measured offset within amplifier 31. The assumption is then made that the offset within amplifier 23 is the same or nearly the same.

Sample introduction. Next the system is readied for introduction of the sample in the cell 22. Switches 33, 35 are on and switch 34 is off. When current flows, this is an indication that the sample has been introduced. In an exemplary embodiment the sample is human blood (or a reference solution for calibration) and the cell 22 contains a glucose oxidase.

Recalibration. During this phase the switches remain as previously set. The PWM is adjusted as needed to give rise to the desired applied voltage, defined as the difference between the voltages at 37 and 38. The voltage at 28 should be stable. Changes in the voltage at 32 are monitored as this affects the applied voltage. The current through the cell 22 is measured (by noting the voltage at 29).

Amperometry. For the amperometry phase, the switches are as before. The PWM monitors the voltages at 32 and 28 to ensure that the applied voltage at the cell 22 is at the desired level. The current through the cell 22 is measured as before.

Potentiometry. Switches 33, 35 are turned off. Switch 34 is turned on. The system measures the potential difference between the working and counter electrodes 37, 38 (the cell voltage), by measuring the voltages at 29 and 28. The difference between those two voltages (plus two times the offset) is the measure of the cell voltage.

This approach uses inexpensive components and thus helps to minimize cost.

Those skilled in the art will have no difficulty devising myriad obvious improvements and variations upon the embodiments of the invention without departing from the invention, all of which are intended to be encompassed by the claims which follow.

What is claimed is:

1. A method for maintaining a desired excitation voltage from a potentially unstable voltage source to a first electrode of an electrochemical cell comprising first and second electrodes, said method comprising the steps of:
   (a) performing a calibration step comprising applying an excitation voltage from the voltage source to the first and second electrodes in each of a plurality of successive steps to arrive by successive approximation at a digital control signal for the voltage source that produces the desired voltage to be applied to the electrodes; and
   (b) applying the digital control signal to the voltage source to maintain the excitation voltage at the desired level.

2. A method for electrochemical measurement of an analyte in a sample comprising the steps of:
   (a) calibrating an electrochemical device comprising a potentially unstable voltage source and first and second electrodes of an electrochemical cell, said calibration step comprising applying an excitation voltage from the voltage source to the first and second electrodes in each of a plurality of successive steps to arrive by successive approximation at a digital control signal for the voltage source that produces a desired voltage to be applied to the electrodes;
   (b) introducing the sample into the electrochemical cell;
   (c) applying the desired voltage to the first electrode using the digital control signal determined in step (a); and
   (d) measuring current between the electrodes as an indication of the amount of analyte in the sample.

3. The method of claim 2, further comprising a recalibration step performed after step (b) and before step (d), said recalibration step comprising the steps of applying an excitation voltage from the voltage source to the first and second electrodes in each of a plurality of successive steps to arrive by successive approximation at an updated digital control signal for the voltage source that produces the desired voltage to be applied to the electrodes in the presence of the sample and using the updated digital control signal to apply voltage for measurement of current in step (d).

4. The method of claim 3, wherein the sample is a liquid sample.

* * * * *